United States Patent
Gleason

(10) Patent No.: US 11,439,515 B2
(45) Date of Patent: Sep. 13, 2022

(54) VARIABLE LORDOTIC ANGULAR EXPANDING IMPLANT WITH CENTRALIZED GRAFT DEPLOYMENT CHANNEL

(71) Applicant: Spineology Inc., St. Paul, MN (US)

(72) Inventor: Joseph Gleason, Eagan, MN (US)

(73) Assignee: Spineology Inc., St. Paul, MN (US)

( * ) Notice: Subject to any disclaimer, the term of this patent is extended or adjusted under 35 U.S.C. 154(b) by 0 days.

(21) Appl. No.: 16/984,005

(22) Filed: Aug. 3, 2020

(65) Prior Publication Data

US 2021/0030561 A1    Feb. 4, 2021

Related U.S. Application Data

(60) Provisional application No. 62/881,509, filed on Aug. 1, 2019.

(51) Int. Cl.
*A61F 2/44* (2006.01)
*A61F 2/30* (2006.01)

(52) U.S. Cl.
CPC .......... *A61F 2/4455* (2013.01); *A61F 2/4425* (2013.01); *A61F 2002/30428* (2013.01); *A61F 2002/30433* (2013.01); *A61F 2002/443* (2013.01)

(58) Field of Classification Search
CPC combination set(s) only.
See application file for complete search history.

(56) References Cited

U.S. PATENT DOCUMENTS

| | | | | |
|---|---|---|---|---|
| 9,801,734 B1* | 10/2017 | Stein | | A61F 2/447 |
| 10,278,830 B1* | 5/2019 | Walker | | A61F 2/447 |
| 2017/0056197 A1* | 3/2017 | Weiman | | A61F 2/4611 |
| 2017/0105844 A1* | 4/2017 | Kuyler | | A61F 2/4601 |
| 2017/0119542 A1* | 5/2017 | Logan | | A61F 2/442 |
| 2018/0296361 A1* | 10/2018 | Butler | | A61F 2/442 |

\* cited by examiner

*Primary Examiner* — Ellen C Hammond
(74) *Attorney, Agent, or Firm* — Skaar Ulbrich Macari, P.A.

(57) ABSTRACT

Provided is a variable lordotic expanding implant with a centralized graft deployment delivery channel (tube) with (or without) an expanding footprint mesh component which is deployed by graft material injection.

14 Claims, 9 Drawing Sheets

VARIABLE LORDOTIC ANGULAR EXPANDING IMPLANT WITH CENTRALIZED GRAFT DEPLOYMENT CHANNEL

PRIORITY

This application claims the benefit of U.S. Provisional Application Ser. No. 62/881,509, filed on Aug. 1, 2019, which is hereby incorporated herein by reference in its entirety.

FIELD

The present invention generally relates to a PEEK spacer/Mesh container hybrid for use in the spine. More particularly, the present invention relates to a PEEK spacer/Mesh container hybrid configured to be placed in the spine via a percutaneous or minimally invasive access opening.

BACKGROUND

PEEK spacers are commonly used in spine surgery, particularly fusion surgery. Often bone graft or other fill material is used with a spacer to help promote bony fusion. It is desirable that the fill material contacts the vertebral endplates while the spacer provides structural support. In an attempt to minimize the size of spacers, traditional PEEK spacers lack adequate cavities for fill material insertion. As such, fill material is often packed around the spacer, rather than in a cavity or cavities of the spacer. Uncontained fill material poses a risk of migrating to surrounding anatomy which can lead to patient injury.

It is desirable to have a spacer small enough to be inserted via a minimally invasive or even percutaneous approach, while allowing for greater fill material containment and fill material contact with the vertebral endplates. There is a continuing need for a PEEK spacer that is small enough to fit through an MIS or percutaneous approach, yet able to expand upon insertion to fully support and/or stabilize the intervertebral space while containing fill material therewithin.

SUMMARY

The present invention, according to certain embodiments, comprises a variable lordotic expanding implant with a centralized graft deployment delivery channel (tube) with (or without) an expanding footprint mesh component which is deployed by graft material injection.

The disclosure includes a surgical implant. A lower platform of the surgical implant is longitudinally elongated. An upper platform is longitudinally elongated and is pivotally connected to the lower platform at a first end thereof. A wedge block is disposed between the upper platform and the lower platform at a second opposing end thereof. A longitudinally elongated graft tube is disposed between the upper platform and the lower platform. A jack screw is disposed through the wedge block with a head of the jack screw facing inward of the upper platform and the lower platform.

Flexible mesh material can be provided to the surgical implant such that the flexible mesh material extends laterally outward from the upper platform and the lower platform to define a container.

The graft tube can comprise a hollow center cavity. A head longitudinal end of the graft tube can comprise threads to engage the jack screw and an aperture can be defined through an opposing tail longitudinal end to allow for a tool to be inserted to engage the head of the jack screw. The graft tube can also comprise a pair of opposing discharge portals defined through a sidewall of the graft tube and facing laterally outward from the surgical implant.

The graft tube can comprise a pair of opposing axle engagement hubs adjacent the tail longitudinal end thereof. The lower platform can define a pair of axle hub engagement slots corresponding to the pair of axle engagement hubs which are sized and shaped to receive the pair of axle engagement hubs therein. The pair of opposing axle engagement hubs can be offset from a longitudinal midline of the graft tube. The upper platform also can define a pair of axle hub engagement slots corresponding to the pair of axle engagement hubs which are sized and shaped to receive the pair of axle engagement hubs therein.

A pair of connecting screws can be provided. Each connecting screw can be disposed through a respective one of the axle engagement hubs, axle engagement slots for the upper platform and the engagement slots for the lower platform. The upper and lower platforms are constrained to pivot about the pair of connecting screws.

The lower platform can define a tool attachment pocket in a longitudinal end thereof.

The upper platform and the lower platform can together define a dovetail longitudinal end that is engaged by the wedge block and a pivoting longitudinal end opposite the dovetail longitudinal end.

An outer longitudinal surface of at least one of the upper platform the lower platform can be textured. The texture can be a saw tooth texture.

Each of the upper platform, the lower platform the wedge block, graft tube and the jack screw can comprise a thermoplastic polymer material such as polyether ether ketone (PEEK), or other biocompatible material.

The implant can be restrained together on a non-pivoting end via dovetailing the upper platform and the lower platform together with the wedge block in interfaced male/female slots.

The disclosure also includes a method of performing spinal fusion surgical procedure. A spinal implant is introduced to a vertebral cavity in a collapsed state. The vertebral cavity is disposed between opposing vertebral endplates. In situ a jack screw that is disposed in a graft tube of the implant and a wedge block that engages a longitudinal end of the spinal implant is turned to draw the wedge block inward of the spinal implant to pivot an upper platform of the spinal implant relative to a lower platform of the spinal implant. The pivot point is adjacent a longitudinal end of the spinal implant opposite the longitudinal end that engages the wedge block. Fill material is introduced in situ into the spinal implant, the fill material passing through the graft tube and outward into a flexible container defined by flexible mesh material provided to lateral sides of the spinal implant. The spinal implant can be is introduced to the vertebral cavity in the collapsed state via a percutaneous surgical path or a minimally invasive surgical path.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

Figure 1:
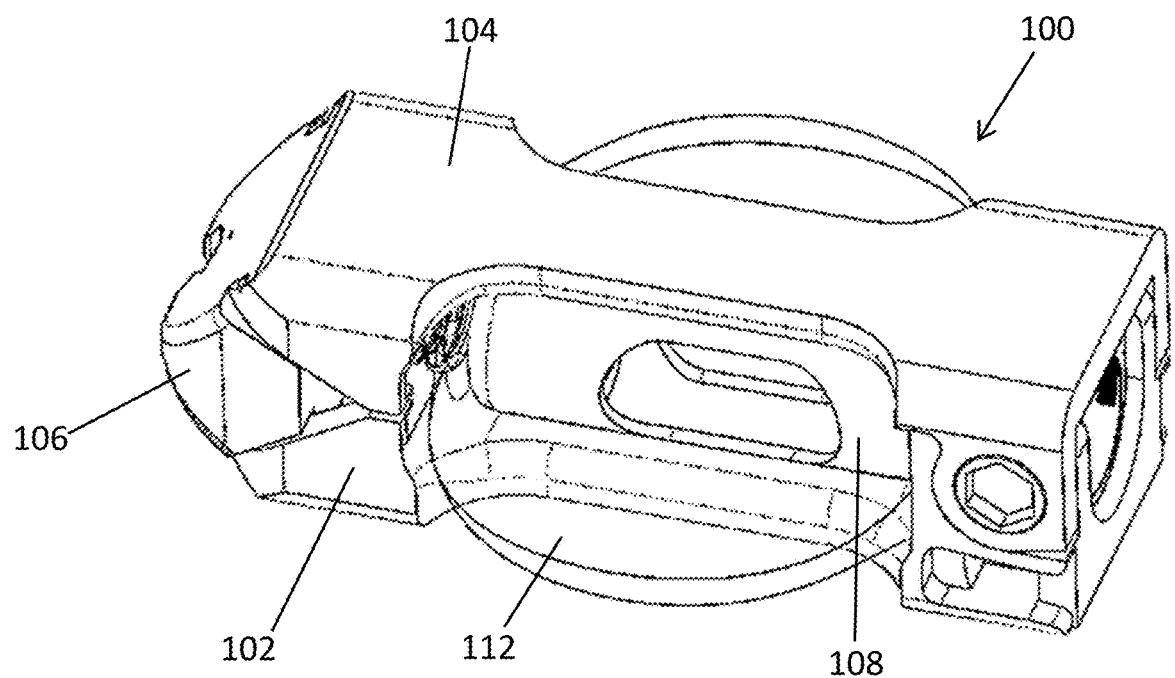
FIG. 1 is a perspective view of an implant according to certain embodiments of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims. For illustrative purposes, cross-hatching, dashing or shading in the figures is provided to demonstrate sealed portions and/or integrated regions or devices for the package.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

Both U.S. Pat. Nos. 9,844,444 B2 and 10,111,756 B2 are hereby incorporated by reference in their entirety herein as part of this application.

FIGS. 1-17 illustrate an implant 100 in a first embodiment in its contracted and expanded state, respectively. The implant generally comprises a lower platform 102, an upper platform 104 pivotally connected to the lower platform 102 at one end thereof, a wedge block 106 that engages the non-pivoting end of the implant, a graft tube 108 disposed longitudinally between the upper and lower platforms, and a jack screw 110 disposed through the wedge block and into the graft tube so that the wedge's position can be adjusted longitudinally between the upper and lower platforms to selectively pivot and expand the implant 100 in the vertical direction (i.e., towards the opposing vertebral end plates).

Figure 2:
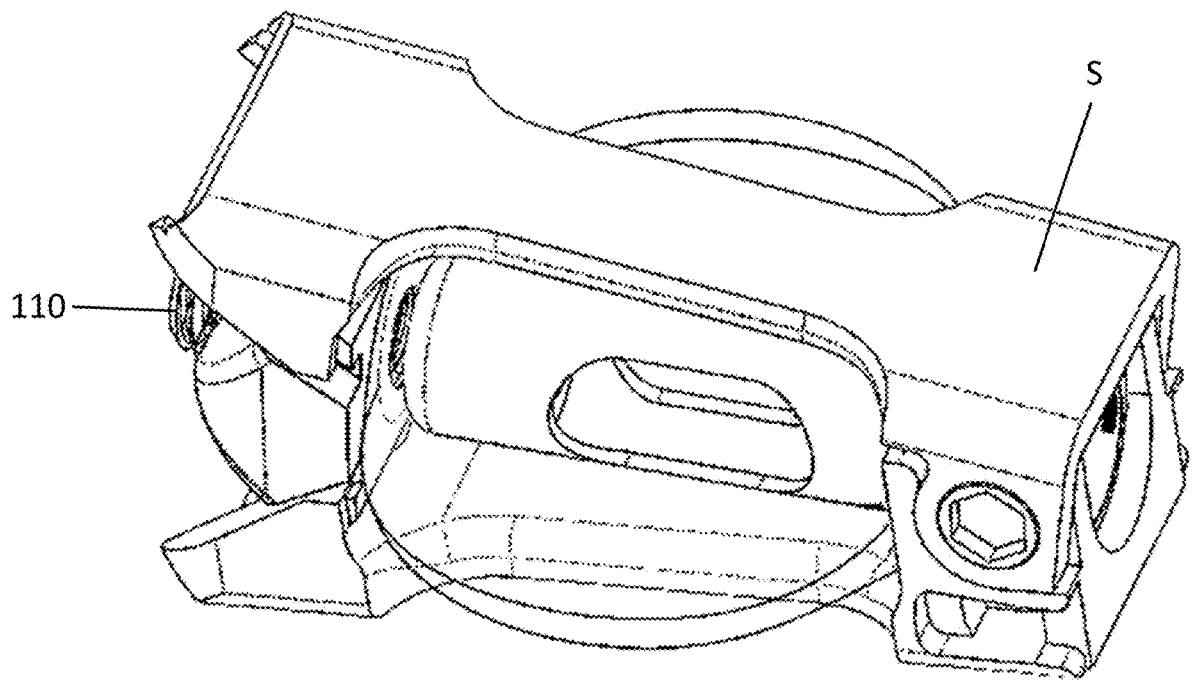
FIG. 2 is another perspective view of an implant according to certain embodiments of the present invention.
Figure 3:
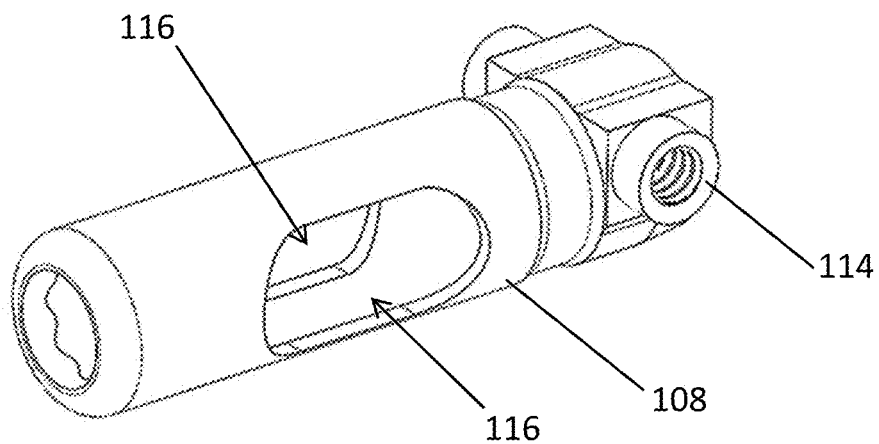
FIG. 3 is a perspective view of a graft tube of an implant according to certain embodiments of the present invention.
Figure 4:
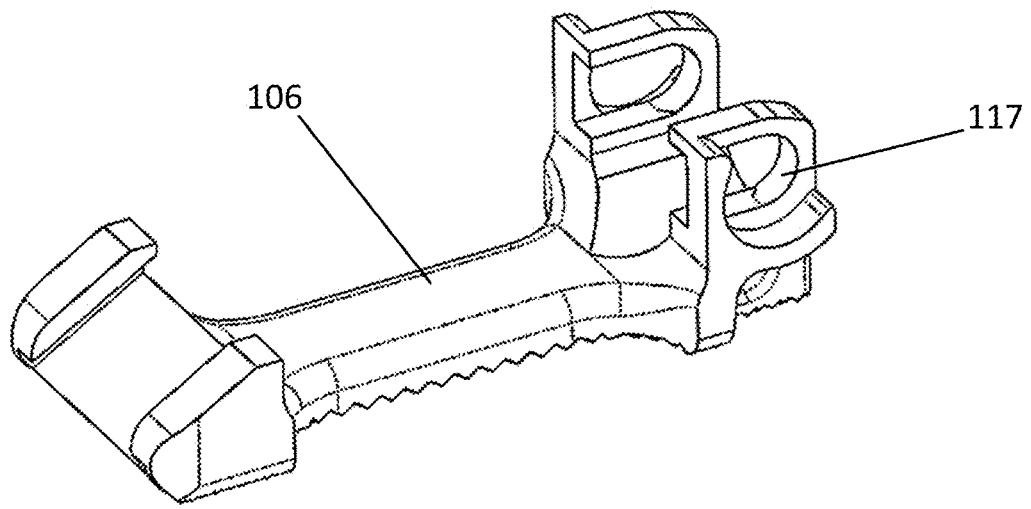
FIG. 4 is a perspective view of a lower platform of an implant according to certain embodiments of the present invention.
Figure 5:
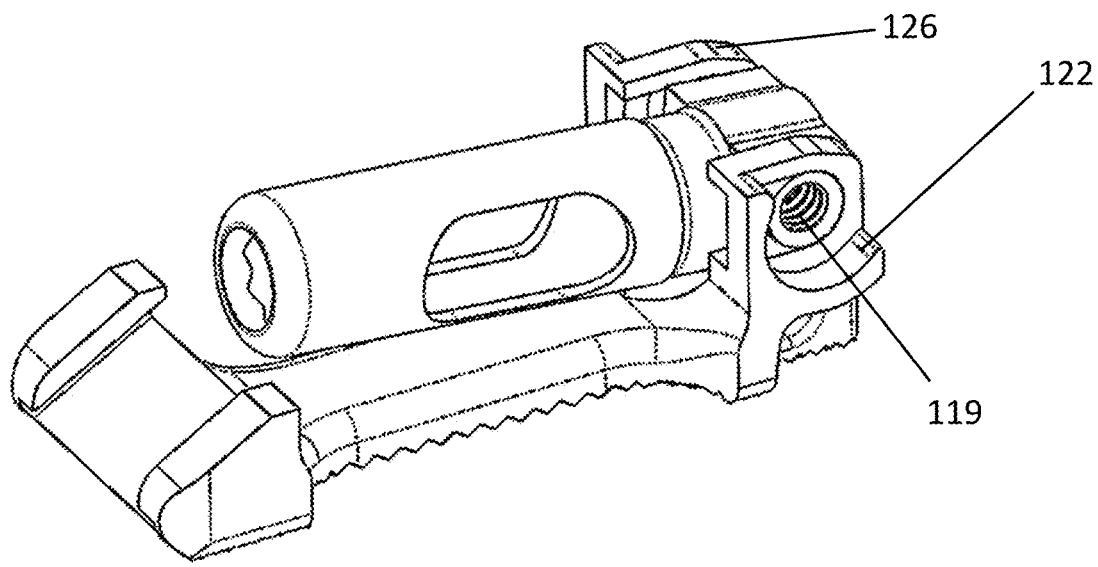
FIG. 5 is a perspective view of a lower platform and graft tube of an implant according to certain embodiments of the present invention.
Figure 6:
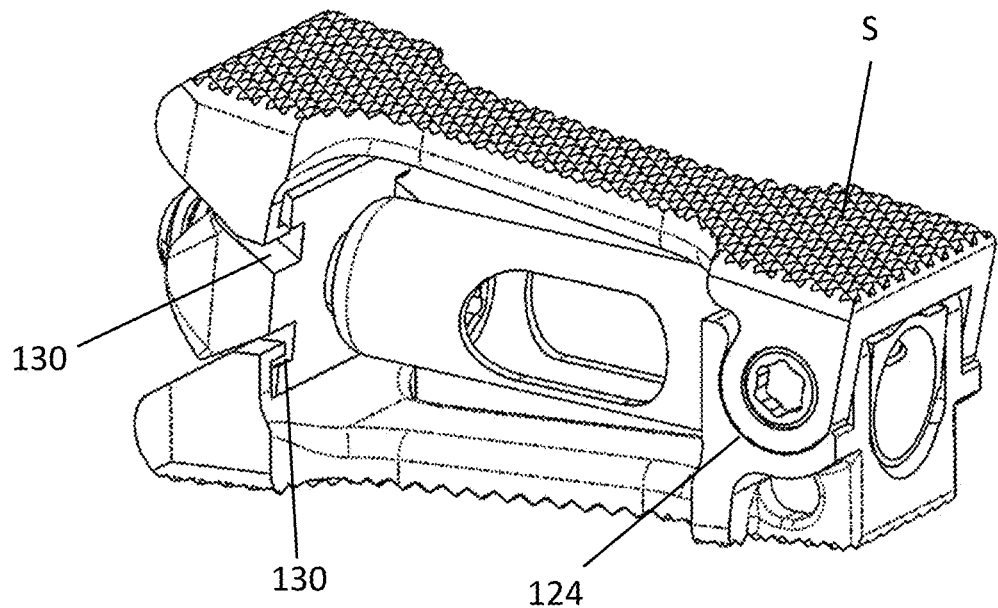
FIG. 6 is a perspective view of a portion of an implant according to certain embodiments of the present invention.
Figure 7:
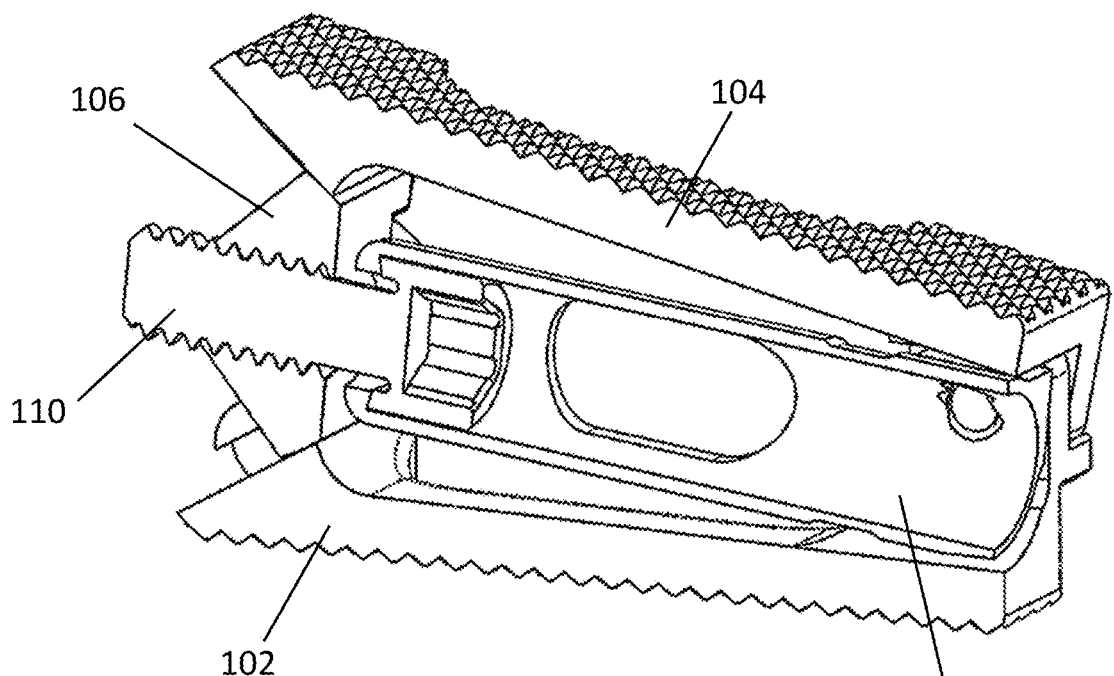
FIG. 7 is a perspective longitudinal cross-sectional view of a portion of an implant according to certain embodiments of the present invention.
Figure 8:
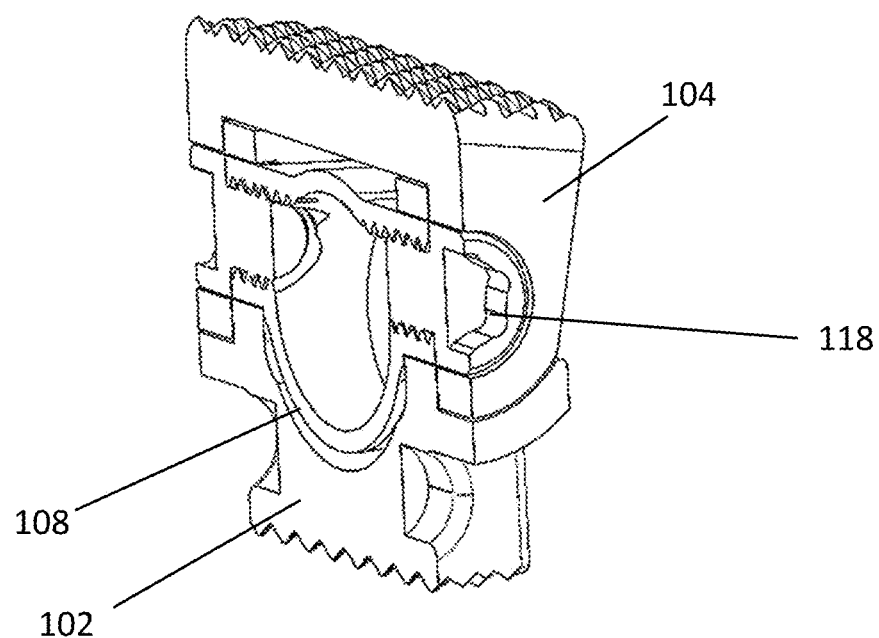
FIG. 8 is a perspective lateral cross-sectional view of a portion of an implant according to certain embodiments of the present invention.
Figure 9:
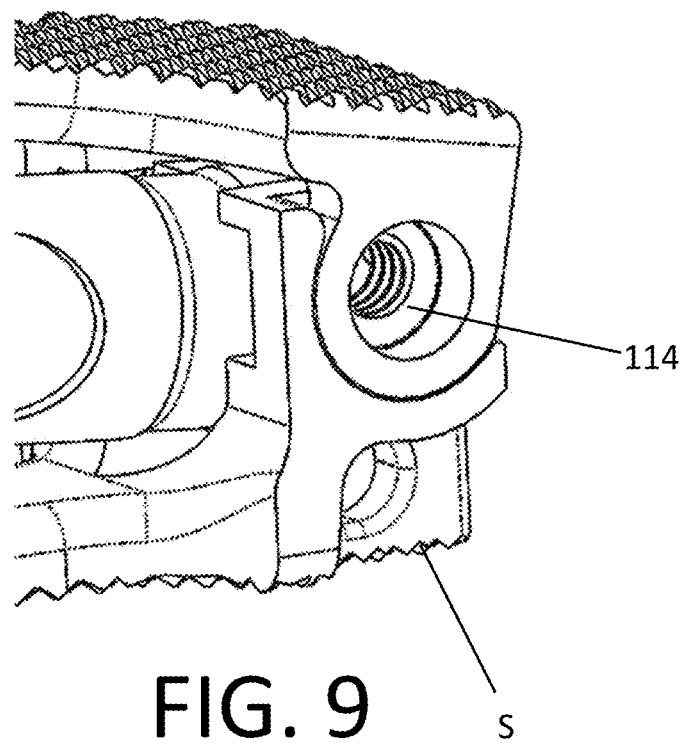
FIG. 9 is a perspective view of a portion of an implant in a contracted state according to certain embodiments of the present invention.
Figure 10:
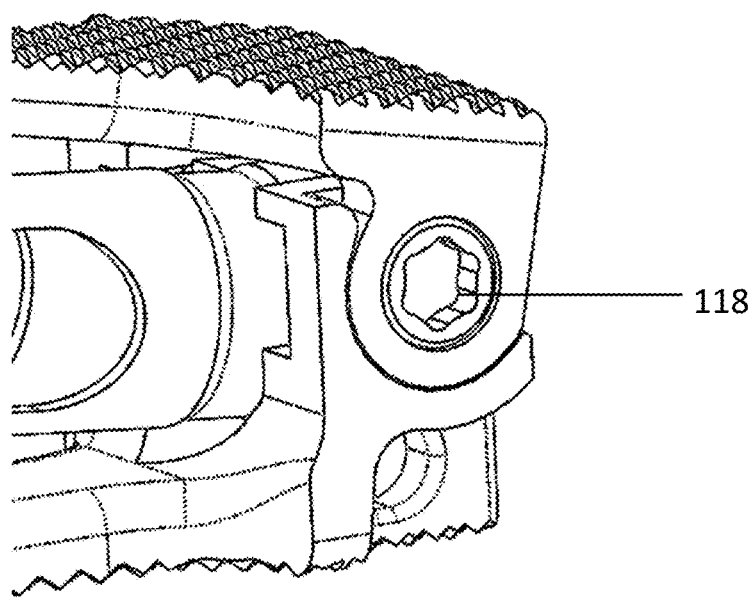
FIG. 10 is a perspective view of a portion of an implant in an expanded state according to certain embodiments of the present invention.
Figure 11:
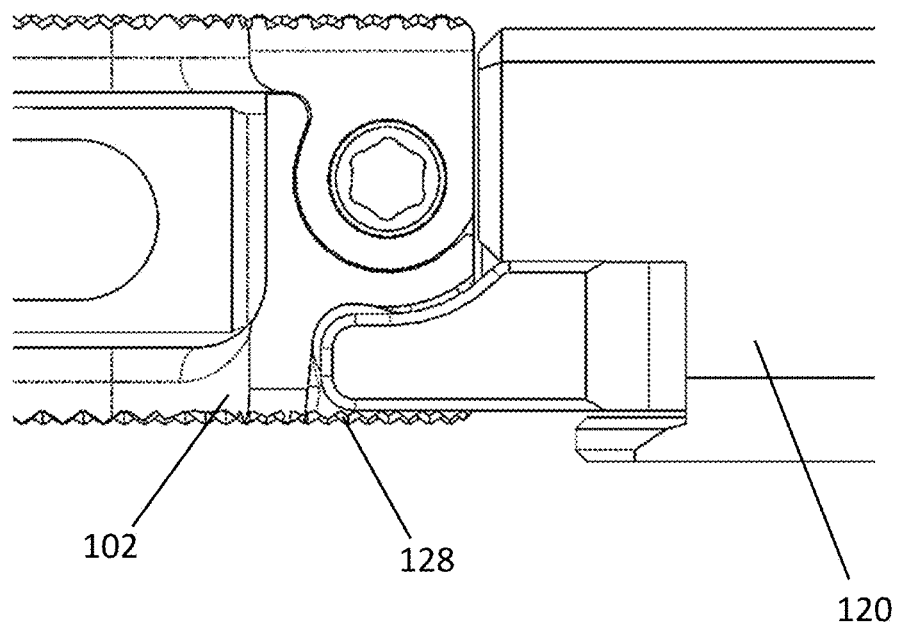
FIG. 11 is a partial side view of an implant in a contracted state according to certain embodiments of the present invention.
Figure 12:
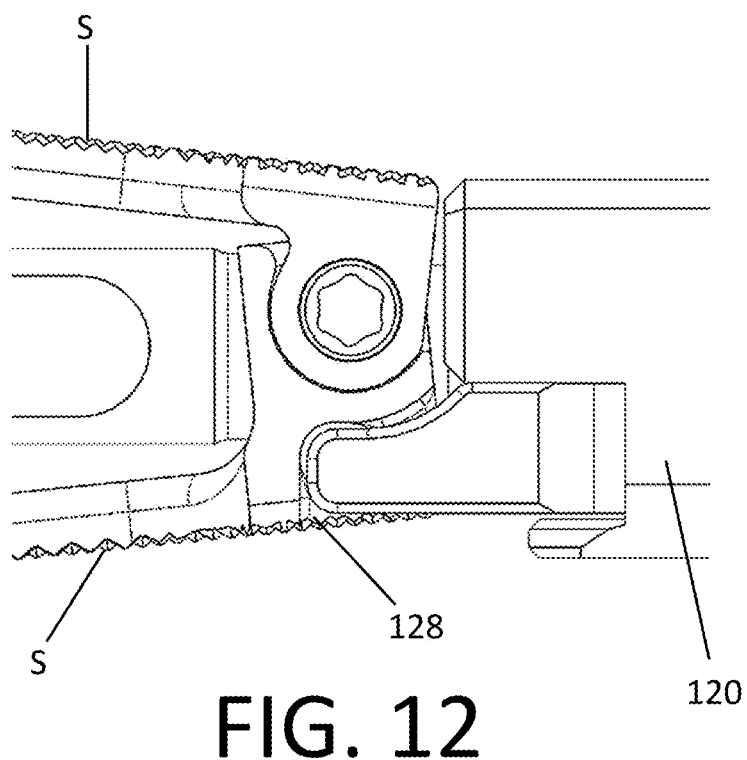
FIG. 12 is a partial side view of an implant in an expanded state according to certain embodiments of the present invention.
Figure 13:
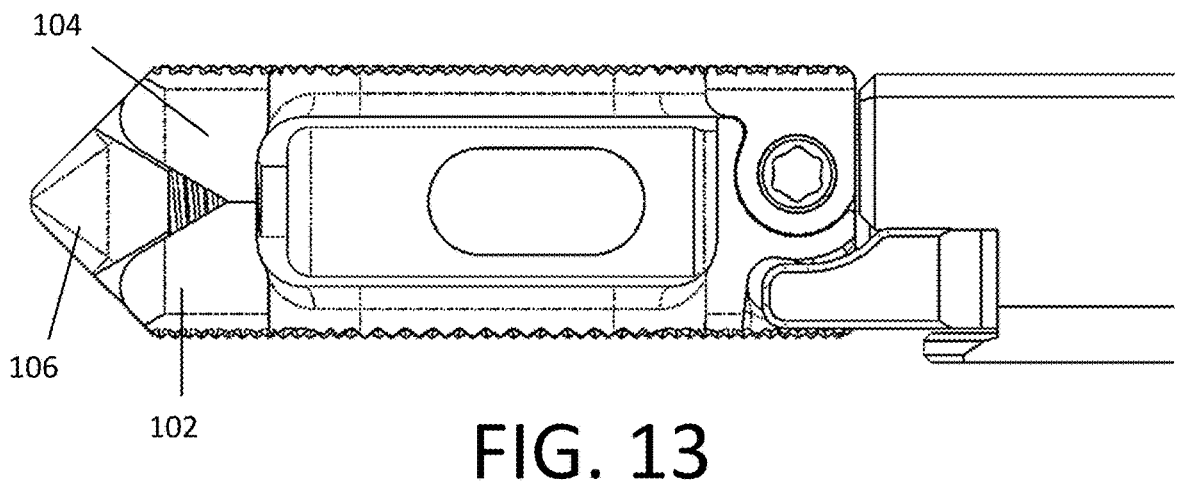
FIG. 13 is a side view of an implant in a contracted state according to certain embodiments of the present invention.
Figure 14:
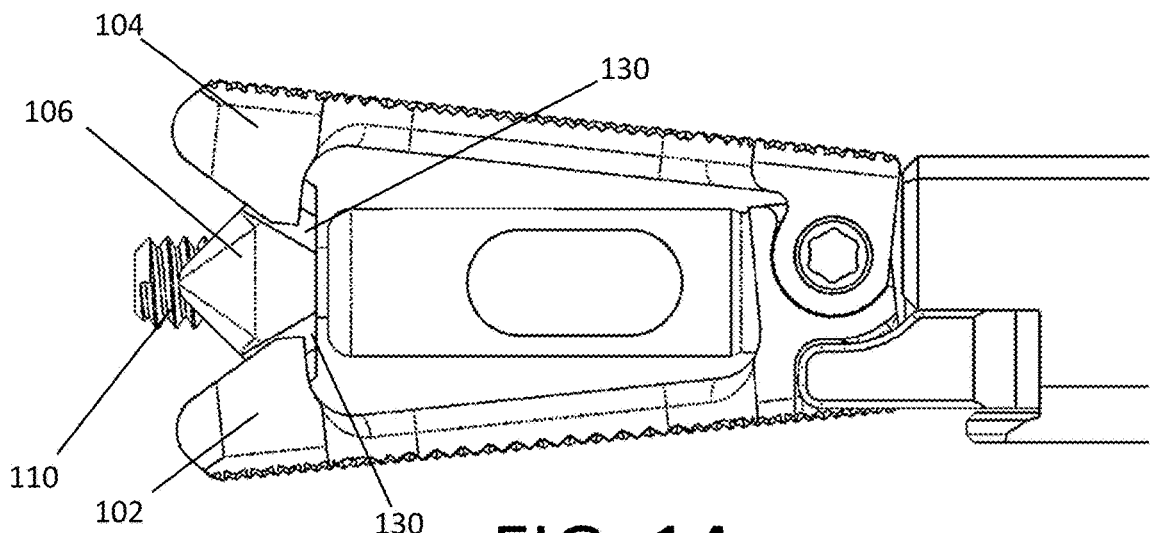
FIG. 14 is a side view of an implant in an expanded state according to certain embodiments of the present invention.
Figure 15:
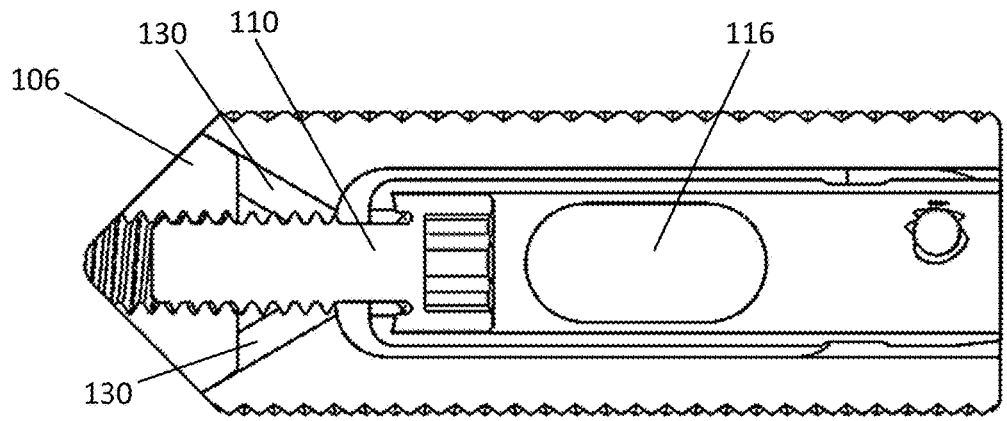
FIG. 15 is a longitudinal cross-section side view of an implant in a contracted state according to certain embodiments of the present invention.
Figure 16:
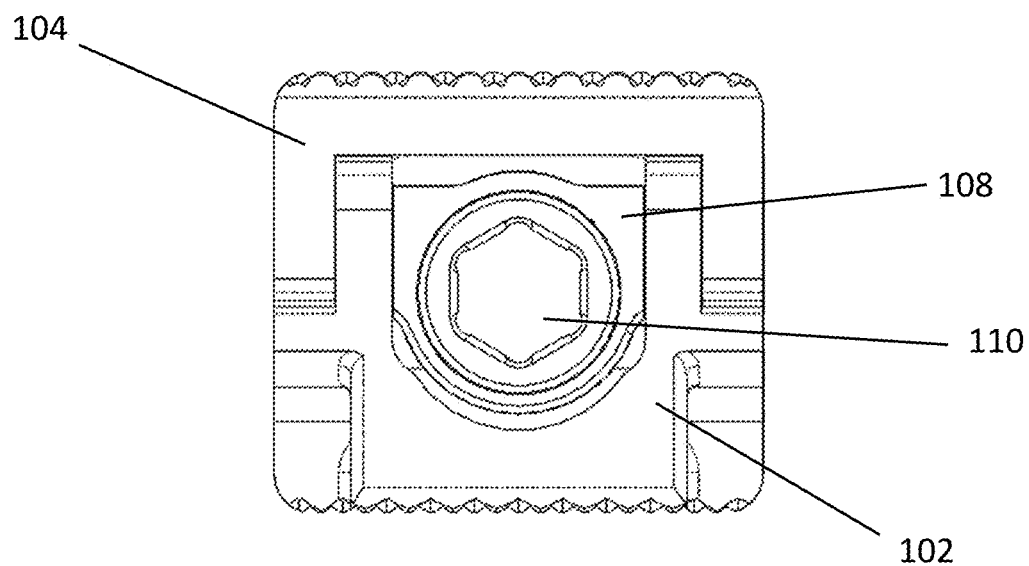
FIG. 16 is an end view of an implant in a contracted state according to certain embodiments of the present invention.
Figure 17:
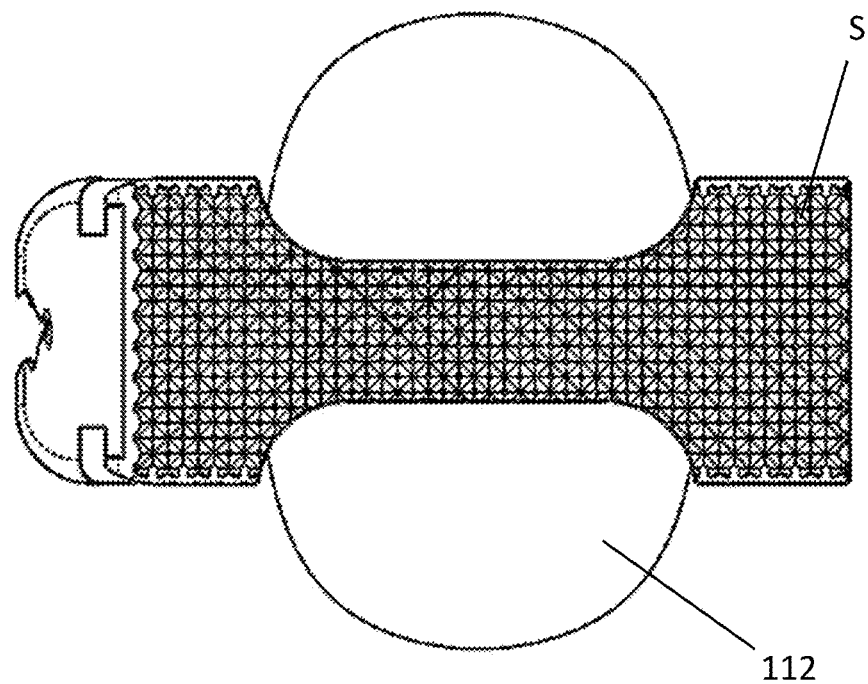
FIG. 17 is a top view of an implant according to certain embodiments of the present invention.

Flexible mesh material is provided to the lateral sides of the implant as shown in FIGS. 1-2 and 17 to define a container 112 for receiving bone graft, bone substitute or any other biocompatible fill material. Such fill material may promote bony fusion. The mesh material used to form the container 112 may be sufficiently porous to allow the fill material to contact the vertebral endplates, promoting bony fusion, while retaining the fill material to prevent migration.

The centralized graft tube 108 comprises a hollow center cavity. The cavity houses the head of the jack screw 110 which the user can turn to contract or draw in the wedge block 106 longitudinally inward of the implant to thereby pivot the upper 104 and lower 102 platforms to expand the implant in the vertical direction.

The opposing end of the centralized graft tube 108 defines axle engagement hubs 114 which are offset from the center line of the tube to allow for adequate attachment real estate in the lower platform 102 for insertion tool attachment. The graft tube 108 also defines discharge portals 116 for graft or fill material deployment.

The lower platform 102 has unique geometry which allows the centralized tube 108 to be installed into internal slots 117 to the pivot point, then restrained in the pivot position by assembly of the top platform 104 with connecting screws 118 inserted through a common screw aperture 119 that extends laterally through the assembly.

The upper 104 and lower 102 platforms nest together at the pivot end with concentric matching geometries allowing compressive loads to be transmitted from the upper platform 104 through the lower platform 102, thereby reducing stress transmission through the connecting screws 118. The lower platform 102 defines an arcuate cam surface 122 that engages the inward facing curved perimeter 124 of the upper platform 104. In a mirrored manner, the upper platform defines a curved cam surface that engages the outward curved perimeter 126 of the lower platform 102.

Referring to FIGS. 11-14, the lower platform 102 defines an insertion tool attachment pocket 128 in the pivot end thereof. The insertion tool attachment pocket 128 allows the lower platform 102 to pivot as the lordotic angle changes, thereby allowing the central tube 108 to remain coaxial with the insertion tool 120.

The upper platform 104, lower platform 102, and wedge (cam) block 106 are dovetailed together on the non-pivoting end of the implant 100 with interfaced male/female slots 130 restraining the implant together in all deployment configurations.

The implant described herein advantageously provides a central fill or graft delivery tube with discharge ports. The expandable mesh container provides for increased footprint after implantation.

Figure 18:
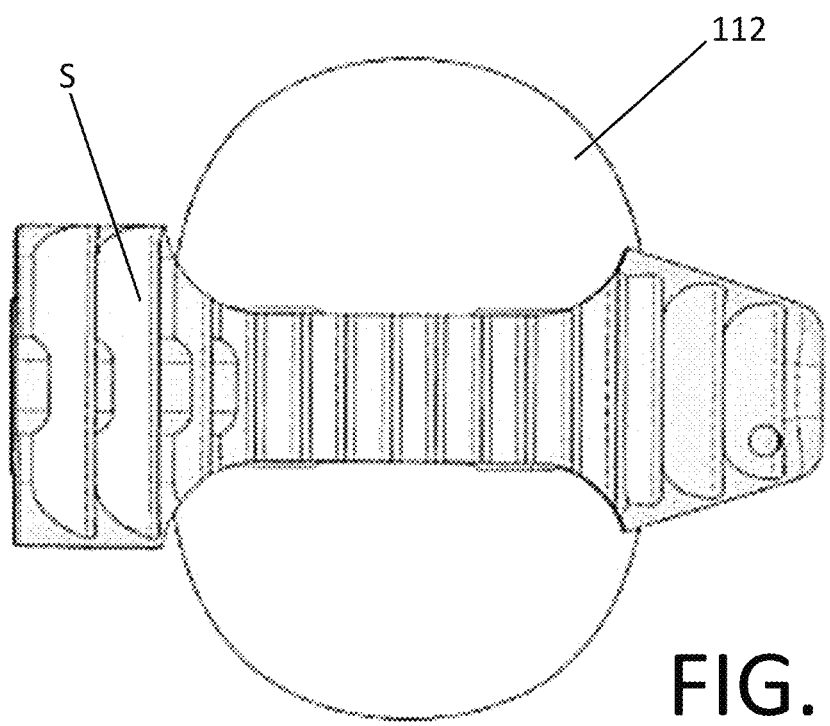
FIG. 18 is a top view of an implant according to certain embodiments of the present invention.
Figure 19:
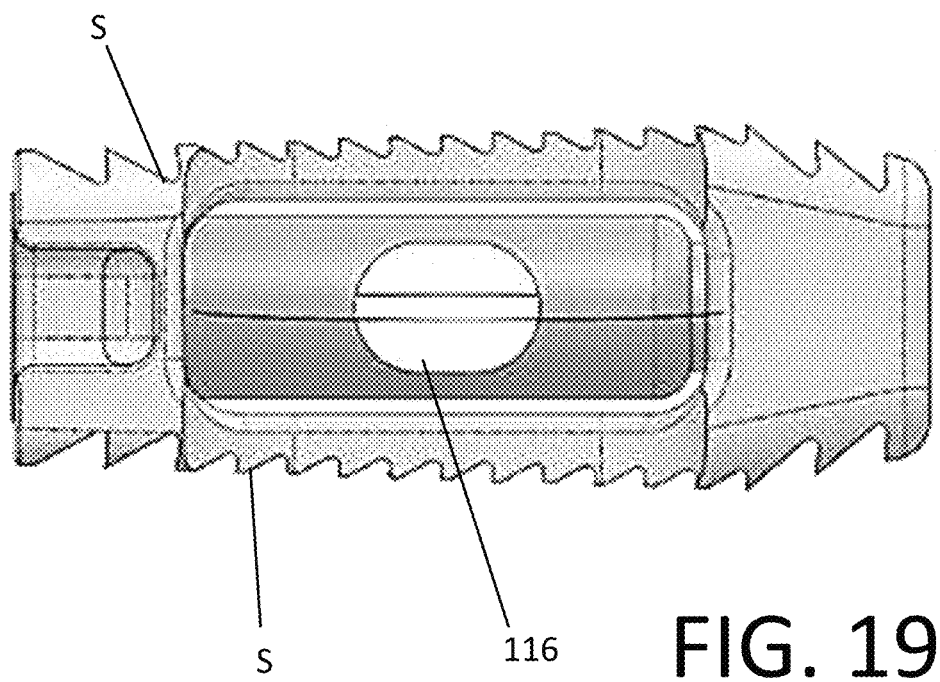
FIG. 19 is a side view of an implant according to certain embodiments of the present invention.

The outer surfaces (S) of the upper 104 and lower 102 platforms (which will contact the vertebral end plates) can be smooth (FIGS. 1-2), textured (FIGS. 4-17) or saw tooth (FIGS. 18-19). Of course, only one or the other upper and lower platform may be textured or saw tooth in further embodiments. Alternative textures can also be employed.

Features of the various embodiments can be mixed and matched to create additional embodiments even if not specifically depicted in one of the figures.

Each of the lower platform 102, the upper platform 104, the wedge block 106, the jack screw 110 and the graft tube 108 may be comprised of PEEK or any other biocompatible material or combination thereof. The container 112 may be comprised of PET or any other biocompatible material or combination thereof. The container 112 may be comprised of material such that the container is flexible and/or conformable to the patient's anatomy.

In use, the implant 100 may be inserted between two vertebrae in a collapsed state and then expanded in situ. Fill material may then be introduced into the container. Introduction of the fill material into the tube flows into the container to fully expand the container.

In use, the implant 100 may be inserted into a prepared intervertebral cavity in a collapsed state. The implant 100 may be inserted with an empty container 112 such that the implant 100 may be placed through a MIS or percutaneous approach. Once placed, container 112 can be expanded and the container 112 filled with fill material.

In one example, the implant is configured to a 25 mm length×10 mm width×8 mm height. However, these dimensions can be varied in other embodiments.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A surgical implant, comprising:
   a lower platform that is longitudinally elongated;
   an upper platform that is longitudinally elongated and is pivotally connected to the lower platform at a first end thereof;
   a wedge block disposed between the upper platform and the lower platform at a second opposing end thereof;
   a longitudinally elongated graft tube disposed between the upper platform and the lower platform, comprising a hollow center cavity, a head longitudinal end, an opposing tail longitudinal end, and a pair of opposing axle engagement hubs adjacent the tail longitudinal end;
   a jack screw disposed through the wedge block with a head of the jack screw facing inward of the upper platform and the lower platform; and
   a pair of connecting screws,
   wherein the head longitudinal end of the graft tube comprises threads to engage the jack screw and an aperture is defined through the tail longitudinal end to allow for a tool to be inserted to engage the head of the jack screw,
   wherein the lower platform defines a pair of axle hub engagement slots corresponding to the pair of axle engagement hubs which are sized and shaped to receive the pair of axle engagement hubs therein,
   wherein the upper platform defines a pair of axle hub engagement slots corresponding to the pair of axle engagement hubs which are sized and shaped to receive the pair of axle engagement hubs therein, and
   wherein each connecting screw is disposed through a respective one of the axle engagement hubs, axle engagement slots for the upper platform and the engagement slots for the lower platform, and
   wherein the upper and lower platforms are constrained to pivot about the pair of connecting screws.

2. The surgical implant of claim 1, further comprising flexible mesh material provided to the surgical implant such that the flexible mesh material extends laterally outward from the upper platform and the lower platform to define a container.

3. The surgical implant of claim 1, wherein the graft tube comprises a pair of opposing discharge portals defined through a sidewall of the graft tube and facing laterally outward from the surgical implant.

4. The surgical implant of claim 1, wherein the pair of opposing axle engagement hubs are offset from a longitudinal midline of the graft tube.

5. The surgical implant of claim 1, wherein the lower platform defines a tool attachment pocket in a longitudinal end thereof.

6. The surgical implant of claim 1, wherein the upper platform and the lower platform together define a dovetail longitudinal end that is engaged by the wedge block and a pivoting longitudinal end opposite the dovetail longitudinal end.

7. The surgical implant of claim 1, wherein an outer longitudinal surface of at least one of the upper platform and the lower platform are textured.

8. The surgical implant of claim 1, wherein an outer longitudinal surface of at least one of the upper platform and the lower platform are saw tooth textured.

9. The surgical implant of claim 1, wherein each of the upper platform, the lower platform, the wedge block, the graft tube and the jack screw comprise PEEK.

10. The surgical implant of claim 1, wherein the upper platform and the lower platform are each dovetailed together with the wedge block on a non-pivoting end of the implant via interfaced male/female slots.

11. A method of performing spinal fusion surgical procedure, comprising:
    introducing a spinal implant to a vertebral cavity in a collapsed state, the vertebral cavity disposed between opposing vertebral endplates;
    turning in situ a jack screw that is disposed in a graft tube of the implant and a wedge block that engages a longitudinal end of the spinal implant to draw the wedge block inward of the spinal implant to pivot an upper platform of the spinal implant outwardly relative to a lower platform of the spinal implant, wherein the pivot point is adjacent a longitudinal end of the spinal implant opposite the longitudinal end that engages the wedge block; and introducing fill material in situ into the spinal implant, passing the fill material through the graft tube and outward into a flexible container defined by flexible mesh material provided to lateral sides of the spinal implant.

12. The method of claim 11, wherein the spinal implant is introduced to the vertebral cavity in the collapsed state via a percutaneous surgical path.

13. The method of claim 11, wherein the spinal implant is introduced to the vertebral cavity in the collapsed state via a minimally invasive surgical path.

14. The method of claim 11, further comprising restraining the implant together on a non-pivoting end via dovetailing the upper platform and the lower platform together with the wedge block in interfaced male/female slots.

* * * * *